US012797244B2

(12) United States Patent
Robins et al.

(10) Patent No.: US 12,797,244 B2
(45) Date of Patent: Nov. 17, 2026

(54) EYE SAFETY FRAMES

(71) Applicant: KITCHEN BLOCKERS INC., King City (CA)

(72) Inventors: Brad Robins, King City (CA); David H. Katz, Thornhill (CA); Shane Katz, Thornhill (CA); Adam Hennick, Montreal (CA)

(73) Assignee: KITCHEN BLOCKERS INC., King City (CA)

( * ) Notice: Subject to any disclaimer, the term of this patent is extended or adjusted under 35 U.S.C. 154(b) by 0 days.

(21) Appl. No.: 19/245,559

(22) Filed: Jun. 23, 2025

(65) Prior Publication Data

US 2026/0224404 A1 Aug. 6, 2026

Related U.S. Application Data

(63) Continuation-in-part of application No. 29/988,449, filed on Feb. 3, 2025.

(51) Int. Cl.
*A61F 9/02* (2006.01)
*A63B 71/10* (2006.01)
*G02C 5/00* (2006.01)

(52) U.S. Cl.
CPC .............. *A61F 9/026* (2013.01); *A63B 71/10* (2013.01); *G02C 5/001* (2013.01)

(58) Field of Classification Search
CPC . A61F 9/02; A61F 9/026; A61F 9/045; A63B 71/10; G02C 5/001; G02C 7/16
(Continued)

(56) References Cited

U.S. PATENT DOCUMENTS 924,613 A * 6/1909 Hellawell ................ A42B 3/20 2/9
1,523,521 A * 1/1925 Goodman .............. A63B 71/10 2/9
(Continued)

FOREIGN PATENT DOCUMENTS

KR 101054176 B1 * 8/2011 ............... G02C 5/16

OTHER PUBLICATIONS

Wikipedia Lensless glasses, https://web.archive.org/web/20240130045509/https://en.wikipedia.org/wiki/Lensless_glasses, Jan. 30, 2024 (Year: 2024).*
(Continued)

*Primary Examiner* — Heather Mangine
(74) *Attorney, Agent, or Firm* — SMART & BIGGAR LP

(57) ABSTRACT

An eye safety frame for protecting the eyes of a wearer includes a pair of ocular frame portions each defining an uncovered ocular space surrounding a corresponding one of the eyes. Each ocular frame portion includes a horizontal top member and a horizontal bottom member. The top and bottom members are joined by a distal side member and a proximal side member and form a generally four-sided closed shape defining the ocular space. The bottom member includes a central portion that curves upwardly toward the top member and outwardly away from the eye. The length of the central portion is more than 50% of the length of the bottom member and the ocular space prevents the ball passing therethrough. A nose bridge portion joins a proximal portion of each ocular frame portion. A pair of elongate arms extend from distal portions of the ocular frame portions toward the wearer's ears.

7 Claims, 7 Drawing Sheets

(58) Field of Classification Search
USPC .......................................................... D16/306
See application file for complete search history.

(56) References Cited

U.S. PATENT DOCUMENTS 1,930,972 A * 10/1933 Griswold .................. A61F 9/04 2/11
2,418,376 A * 4/1947 Turner ................... A63B 71/10 2/9
2,715,222 A * 8/1955 Sowle .................... A63B 71/10 2/9
2,923,943 A * 2/1960 Rubin ...................... G02C 9/04 2/13
3,144,658 A * 8/1964 Byron ..................... A61F 9/045 351/44
D212,199 S * 9/1968 Bloch .......................... D16/306
3,577,566 A * 5/1971 Kislin ..................... A61F 9/045 351/44
3,790,259 A * 2/1974 Leblanc ................. G02C 5/146 351/113
4,229,837 A * 10/1980 Solari .................... A63B 71/10 2/431
4,298,991 A * 11/1981 Recenello ................ G02C 7/16 2/451
4,367,561 A * 1/1983 Solari ..................... A61F 9/026 2/9
4,603,442 A * 8/1986 Barfield .................... A61F 9/02 2/446
D292,101 S * 9/1987 Baptiste ....................... D16/317
D306,604 S * 3/1990 Null ............................ D16/315
4,934,807 A * 6/1990 Bolle ...................... A61F 9/026 351/44
4,999,855 A * 3/1991 Brown ................... A63B 71/10 2/909
D316,104 S * 4/1991 Reynolds ..................... D16/325
5,208,614 A * 5/1993 Jannard ..................... A61F 9/02 351/158
5,412,438 A * 5/1995 Bolle' .................... G02C 5/126 351/44
D365,593 S * 12/1995 Leonardi ...................... D16/330
5,495,623 A * 3/1996 Leonardi ................ G02C 11/00 2/431
D372,256 S * 7/1996 Tabacchi ...................... D16/306
5,555,038 A * 9/1996 Conway ................. G02C 5/126 351/44
5,644,800 A 7/1997 Leonardi
5,790,230 A * 8/1998 Sved ....................... A61F 9/025 351/110
5,956,115 A * 9/1999 Bolle ....................... G02C 5/00 351/44
5,969,786 A * 10/1999 Marcum ................ G02C 5/008 351/63
D421,448 S * 3/2000 Chen ............................ D16/306
6,062,688 A * 5/2000 Vinas ..................... G02C 11/08 351/44
6,247,811 B1 * 6/2001 Rhoades ................. A61F 9/027 2/431
6,292,955 B1 * 9/2001 Anton ..................... A61F 9/025 2/441
6,308,711 B1 * 10/2001 Goldberg .................. A61F 9/02 128/858
6,758,562 B1 * 7/2004 Barnette .................. G02C 5/16 351/114
D588,622 S * 3/2009 Magal .......................... D16/306
D617,366 S * 6/2010 Fulton .......................... D16/337
7,828,428 B1 * 11/2010 Livingston ............. G02C 5/005 351/159.67
D638,050 S * 5/2011 Mage ........................... D16/326
D694,315 S * 11/2013 Junge ........................... D16/101
D697,129 S * 1/2014 Morrison ..................... D16/101
D746,360 S * 12/2015 Junge ........................... D16/326
9,897,821 B2 2/2018 Janisse et al.
10,394,047 B2 * 8/2019 DiChiara ............... G02C 5/126
12,239,579 B2 * 3/2025 Calilung .................. G02C 9/00
2003/0035082 A1 * 2/2003 Olney ..................... A61F 9/026 351/62
2004/0017539 A1 * 1/2004 Nagata ................... G02C 7/088 351/57
2004/0133958 A1 * 7/2004 Darnell .................. A63B 71/10 2/15
2006/0117449 A1 * 6/2006 Hahn ....................... A42B 3/20 2/9
2006/0132704 A1 * 6/2006 Gait ........................ A61F 9/029 2/424
2007/0182916 A1 * 8/2007 Blanshay ................ A61F 9/025 351/62
2008/0013036 A1 * 1/2008 Daems ..................... G02C 5/00 351/41
2009/0178185 A1 * 7/2009 Brine, III ................ A61F 9/026 2/9
2011/0078847 A1 * 4/2011 Hahn ..................... A63B 71/10 2/431
2012/0062832 A1 * 3/2012 Stanley .................... G02C 5/12 351/136
2013/0212784 A1 * 8/2013 Cleva ...................... B32B 3/266 2/413
2013/0298318 A1 * 11/2013 Rogers .................... A61F 9/027 2/439
2014/0026299 A1 * 1/2014 Sumelius ............... A63B 71/10 2/424
2014/0026301 A1 * 1/2014 Brown ................... A63B 71/10 2/439
2015/0273304 A1 * 10/2015 Glynn ................ A63B 69/0002 473/422
2016/0085091 A1 * 3/2016 Chu ......................... G02C 1/02 351/62
2016/0116759 A1 * 4/2016 Janisse .................... A61F 9/029 2/451
2016/0139430 A1 * 5/2016 Rigas ..................... G02C 5/001 2/12
2018/0078420 A1 * 3/2018 Gustafsson .............. G02C 5/20
2018/0267337 A1 * 9/2018 Walker ..................... G02C 5/02
2019/0083301 A1 * 3/2019 DauSchmidt ........... A61F 7/106
2019/0090577 A1 * 3/2019 Stolker .................. A42B 3/185
2019/0377194 A1 * 12/2019 Chen ...................... G02C 5/126
2020/0241326 A1 * 7/2020 Huang ..................... G02C 1/04
2020/0325331 A1 10/2020 Honda et al.
2021/0026156 A1 * 1/2021 Li ........................... G02C 1/08
2021/0072559 A1 * 3/2021 Wang ..................... G02C 11/10
2021/0141246 A1 * 5/2021 Hilton ...................... G02C 9/04
2022/0322767 A1 * 10/2022 Hancock ............ A41D 13/1107
2024/0219751 A1 * 7/2024 Offman .................. G02C 5/001
2024/0369852 A1 * 11/2024 Chen ........................ G02C 1/10

OTHER PUBLICATIONS

Translation of KR 101054176, Sim, Aug. 3, 2011 (Year: 2011).*
Sports Virtuoso. P360 Eyeguards Protective Eyewear Lens less Glasses by Sports Virtuoso, https://sportsvirtuoso.com/products/p360-eyeguards-protective-eyewear-lens-less-glasses, Accessed Online: Dec. 6, 2024, 6 pages.
Kitchenblockers, posted at instagram.com by Shane Katz, posting date Nov. 29, 2024, [online], [site visited Mar. 2, 2026]. Available from Internet, URL: https://www.instagram.com/p/DC9fW2jR17c/ (Year: 2024).

* cited by examiner

EYE SAFETY FRAMES

FIELD OF THE INVENTION

This application relates generally to eye safety frames, and more specifically to sports eye safety frames without lenses that are configured to prevent a ball from contacting the eyes of a wearer.

BACKGROUND

A number of available sports frames include lenses to protect a wearer's eyes from impact with racquet sports balls such as pickleball balls. During play, the known frames may adversely impact the wearer's ability to see the ball for a number of reasons, such as the lenses fogging up or being scratched. Consequently, the wearer's game play may be improved by using eye safety frames without lenses.

SUMMARY

The following summary is provided to introduce the reader to the more detailed discussion to follow. The summary is not intended to limit or define any claimed or as yet unclaimed invention. One or more inventions may reside in any combination or sub-combination of the elements or process steps disclosed in any part of this document including its claims and figures.

In one aspect, an eye safety frame for protecting the eyes of a wearer from a ball is provided. The eye safety frame includes a pair of ocular frame portions and a pair of elongate arms. Each ocular frame portion defines an ocular space surrounding a corresponding one of the eyes and includes an elongate horizontal top member spaced apart from an elongate horizontal bottom member. The top and bottom members are joined by an elongate distal side member spaced apart from an elongate proximal side member. The top member, the bottom member, the proximate side member, and the distal side member form a generally four-sided closed shape defining the ocular space. The ocular space is uncovered. The bottom member includes a central portion that curves upwardly toward the top member and outwardly away from the eye. The ocular space prevents the ball passing therethrough. The length of the of the central portion is more than 50% of the length of the bottom member. A proximal portion of one of the ocular frame portions is joined to the proximal portion of the other of the ocular frame portions by a nose bridge portion. Each one of the pair of elongate arms extends from a distal portion of a corresponding one of the ocular frame portions toward a corresponding one of the ears.

In some examples, the nose bridge portion includes a central section and a pair of adjustable nose wings extending from the central section. The pair of adjustable nose wings are adapted to fit onto the nose.

In some examples, the eye safety frames include one or more resilient cushions extending inwardly from the eye safety frames. In some examples, the one or more resilient cushions are made from an energy absorbing material.

In some examples, the one or more resilient cushions include a central cushion extending inwardly from the nose bridge towards the brow of the wearer.

In some examples, the one or more resilient cushions include of a pair of side cushions. Each one of the pair of side cushions is located on an inner surface of each of the inner arms adjacent to the temple of the use.

It will be appreciated by a person skilled in the art that a method or apparatus disclosed herein may embody any one or more of the features contained herein and that the features may be used in any particular combination or sub-combination.

These and other aspects and features of various embodiments will be described in greater detail below.

BRIEF DESCRIPTION OF THE DRAWINGS

For a better understanding of the described embodiments and to show more clearly how they may be carried into effect, reference will now be made, by way of example, to the accompanying drawings in which.

Figure 1:
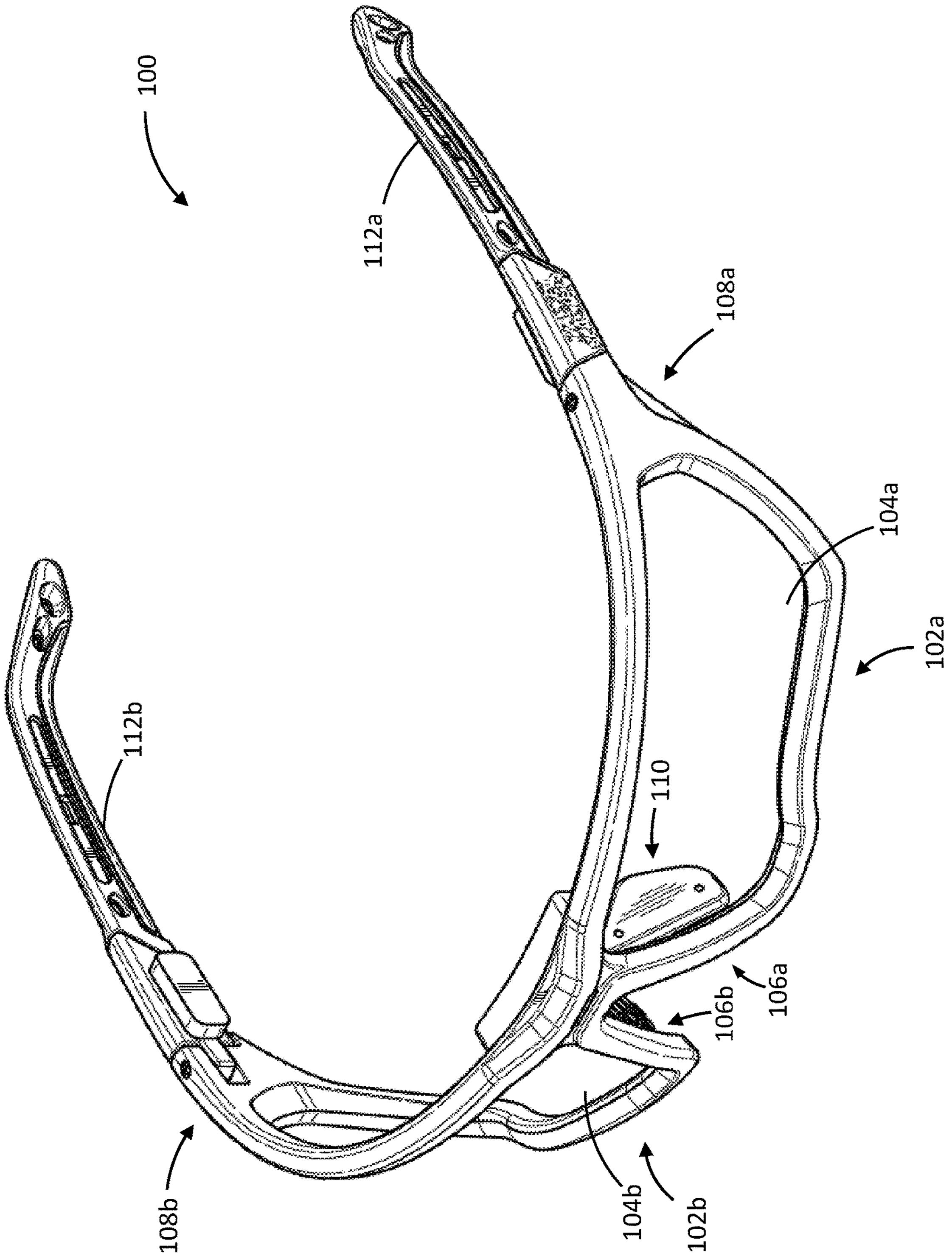
FIG. 1 is a top perspective view of an example eye safety frame.

The drawings included herewith are for illustrating various examples of articles, methods, and apparatuses of the teaching of the present specification and are not intended to limit the scope of what is taught in any way.

DESCRIPTION OF EXAMPLE EMBODIMENTS

Various apparatuses, methods and compositions are described below to provide an example of an embodiment of each claimed invention. No embodiment described below limits any claimed invention and any claimed invention may cover apparatuses and methods that differ from those described below. The claimed inventions are not limited to apparatuses, methods and compositions having all of the features of any one apparatus, method or composition described below or to features common to multiple or all of the apparatuses, methods or compositions described below. It is possible that an apparatus, method or composition described below is not an embodiment of any claimed invention. Any invention disclosed in an apparatus, method or composition described below that is not claimed in this document may be the subject matter of another protective instrument, for example, a continuing patent application, and the applicant(s), inventor(s) and/or owner(s) do not intend to abandon, disclaim, or dedicate to the public any such invention by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures, and components have not been described in detail so as not to obscure the example embodiments described herein. Also, the description is not to be considered as limiting the scope of the example embodiments described herein.

FIGS. 1-7 illustrate a eye safety frame, referred to generally as 100, for preventing direct contact between a wearer's eyes and a ball while playing sports. The ball may be a ball used in racquet sports such as pickleball. Preferably, the ball is a pickleball ball. The eye safety frames may be made of any suitable material, such as plastic or metal. Preferably, the eye safety frames are made of a material that is resiliently deformable such as a combination of hard and soft plastics.

Referring to FIG. 1, the eye safety frame 100 includes a left ocular frame portion 102*a* and a right ocular frame portion 102*b*. The left ocular frame 102*a* portion defines an uncovered left ocular space 104*a* which is aligned with a wearer's left eye and the right ocular frame portion 102*b* defines an uncovered right ocular space 104*b* which is aligned with a wearer's right eye.

Each ocular frame portion 102*a,b* has a proximal portion 106*a,b* located on its inward facing side, and a distal portion 108 located on its outward side. In the illustrated example, the left ocular frame portion 102*a* has a left proximal portion 106*a* and a left distal portion 108*a*. The right ocular frame portion 102*b* has a right proximal portion 106*b* and a right distal portion 108*b*. Each ocular frame portion 102*a,b* substantially surrounds a corresponding one of the wearer's eyes. When worn by the wearer, the ocular frame portions 102*a,b* form a barrier which protects the wearer's eyes and surrounding area from direct contact with a ball without the need for a lens.

Figure 2:
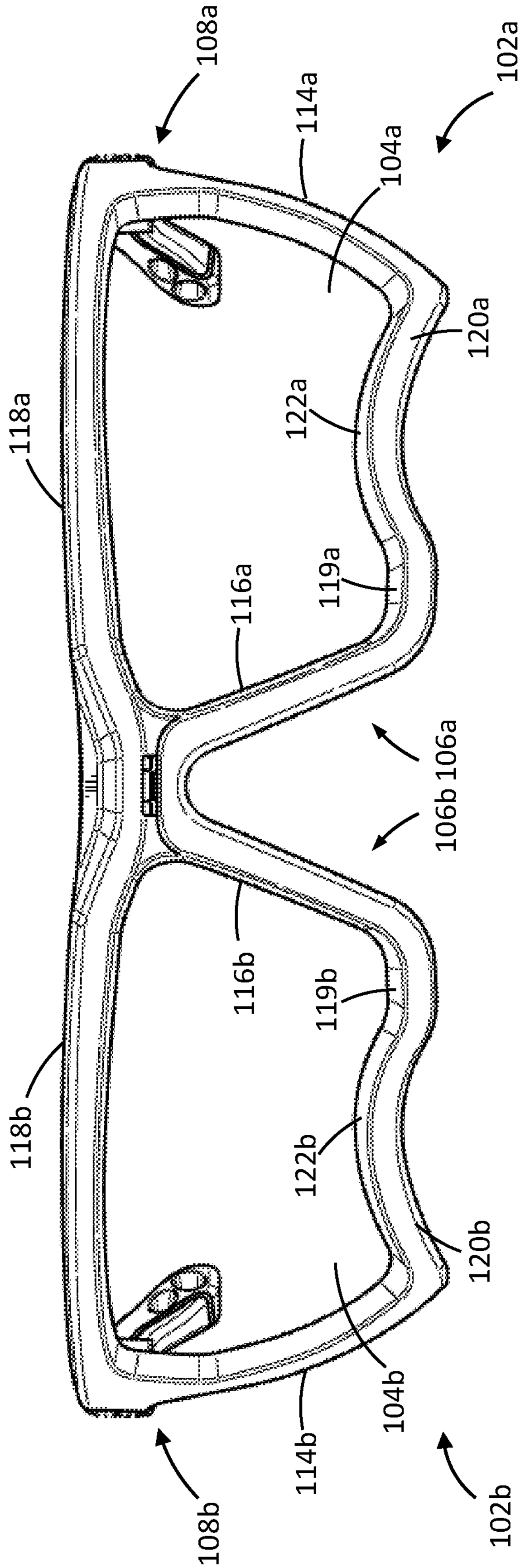
FIG. 2 is a front view of the example eye safety frame shown in FIG. 1.
Figure 3:
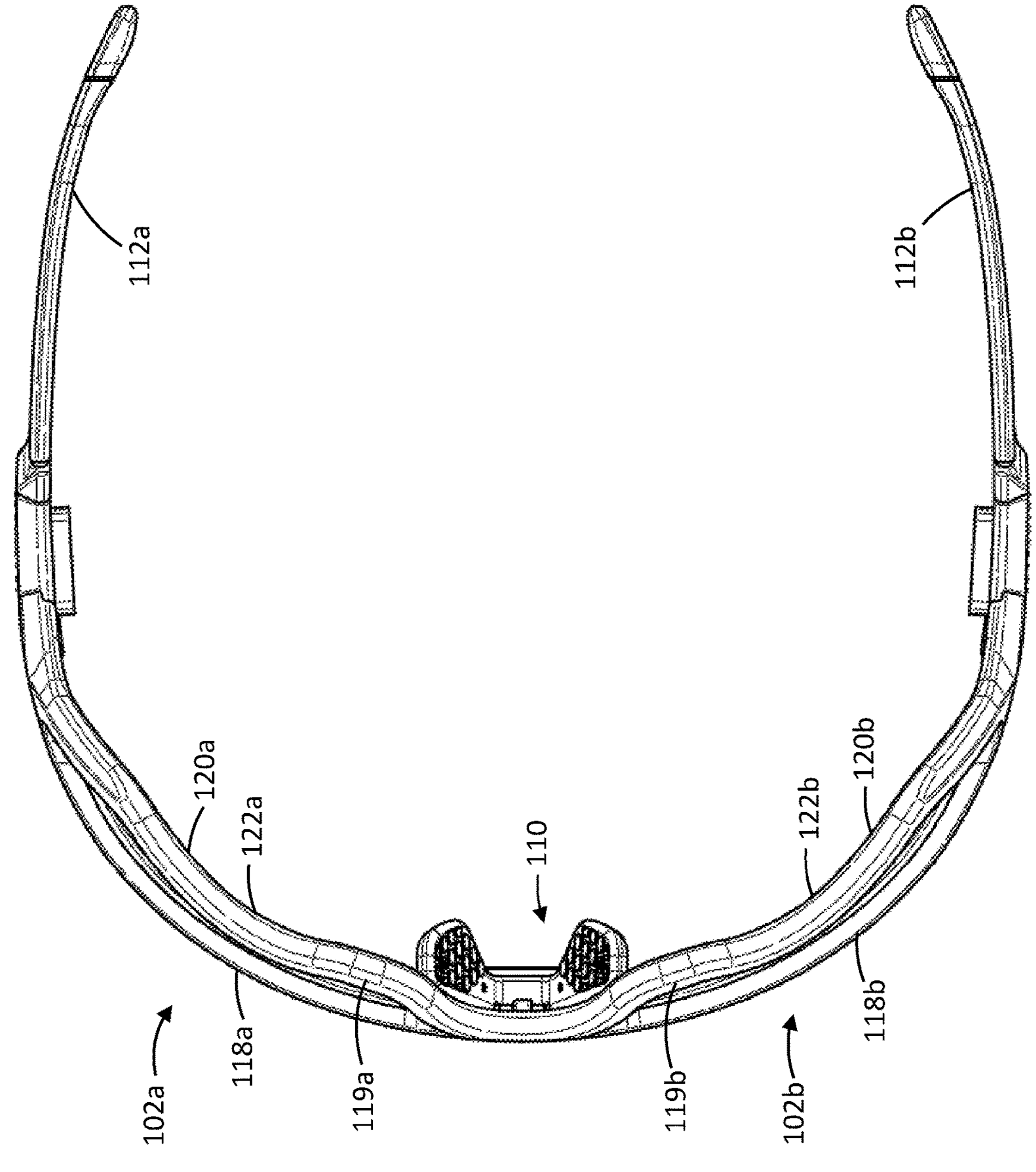
FIG. 3 is a bottom view of the example eye safety frame shown in FIG. 1.

Referring to FIGS. 1-3, the eye safety frame 100 further includes a nose bridge portion 110 extending between and joining the proximal portions 106*a,b* of the left and right ocular frame portions 102*a,b*. The nose bridge portion 110 is adapted to sit on a wearer's nose. Additionally, the eye safety frame 100 includes a left elongate arm 112*a* and a right elongate arm 112*b*. The elongate arms 112*a,b* extend rearwardly from the corresponding distal portions 108*a,b* of the ocular frame portions 102*a,b* towards the wearer's ears. Together, the nose bridge portion 110 and the pair of elongate arms 112*a,b* form three points which are normally in contact with a wearer's nose and ears to hold the eye safety frames 100 securely in position.

Referring to FIG. 2, each of the ocular frame portions 102*a,b* includes a substantially vertical distal elongate side member 114*a,b* on the distal portion 108*a,b* of the ocular frame portion 102,*a,b* and a substantially vertical proximal elongate side member 116*a,b* on the proximal portions 106*a,b* of the ocular frame portion 102*a,b*.

Each of the ocular frame portions 102*a,b* further include an elongate horizontal top member 118*a,b* which joins the upper ends of the distal elongate side member 114*a,b* and the proximal elongate side member 116*a,b* of each ocular frame portion 102*a,b*. Each of the ocular frame portions 102*a,b* also includes an elongate substantially horizontal bottom member 120*a,b* which joins the lower ends of the distal elongate side member 114*a,b* and the proximal elongate side member 116*a,b*. Each of the distal side members 114*a,b*, proximal side members 116*a,b*, top members 118*a,b*, and bottom members 120*a,b* form a four-sided closed shape which defines the shape of each ocular frame portion 102*a,b* and, thereby also defines the shape of the ocular spaces 104*a,b*.

In the illustrated example, the distal elongate side member 114 extends generally vertically from the bottom member 120 to the top member 118 and the proximal elongate side member 116 extends upwardly from the bottom member 120 towards the top member 118 at an angle offset from vertical to define an ocular frame portion 102 and ocular space 104 that are generally trapezoidal in shape. In other examples, the distal side member 114 and the proximal side member 116 may both extend generally vertically from the bottom member 120 to the top member 118 to define an ocular frame portion 102 and ocular space 104 that are generally rectangular in shape. In yet other examples, the distal side member 114 and proximal side member 116 may both extend upwardly from the bottom member 120 at an angle offset from vertical to define an ocular frame portion 102 and ocular space 104 that are trapezoidal in shape.

Referring to the example illustrated in FIG. 2, each elongate horizontal top member 118*a,b* is generally straight and oriented generally horizontally within a vertical plane. Furthermore, as illustrated in FIG. 1 each horizontal top member 118*a,b* may be curved within a horizontal plane to generally follow the curvature of the wearer's face. The curved shape of the eye safety frame 100 allows the frame to "wrap" around the wearer's face. This wrapped configuration improves stability when worn and reduces obstructions to a wearer's peripheral view.

In some alternative examples, each horizontal top member 118*a,b* may be generally straight in both the horizontal plane and vertical plane. In other examples, each horizontal top member 118*a,b* may be oriented at an offset angle from horizontal within the vertical plane. In yet other examples, each horizontal top member 118*a,b* may have a curved top portion. The curved top portion may curve downwardly within the vertical plane towards the bottom member 120 to reduce the ocular space 104, or upwardly away from the bottom member 120 to increase the ocular space 104.

As illustrated in FIG. 2, each elongate bottom member 120*a,b* is generally horizontal within the vertical plane. Furthermore, as illustrated in FIG. 3 each horizontal bottom 120*a,b* member may be curved within the horizontal plane to generally follow the curvature of the wearer's face. Similar to the curve of the top member 118 within the horizontal plane, a bottom member 120 that is curved in the horizontal plane allows for the eye safety frames to wrap around a wearer's head. In other examples, the horizontal bottom member 120 may be generally straight in the horizontal plane.

Referring to FIG. 2, each elongate horizontal bottom member 120*a,b* includes a corresponding central portion 122*a,b*. In the illustrated example, the central portion 122 is greater than 50% of the length of the bottom member 120. In other examples, the central portion 122 may be less than 50% of the length of the bottom member 120. The central portion 122 may be integrally formed with the bottom member 120 or may be a separate component which, together with outer portions, forms the bottom member 120.

Each central portion 122*a,b* is curved upwardly towards the top member 118 to reduce the area of the ocular space 104. More specifically, the ocular space 104 is limited by the curved central portion 122 such that a ball is prevented from passing through the ocular space 104. In the illustrated example, no circular area within the ocular space 104 has a diameter that is the same or larger than the diameter of a ball, such as a pickleball ball. By limiting the ocular space 104, the shape of each central portion 122*a,b* facilitates the ocular space 104 to block a ball from passing through the ocular frame portions 102*a,b* and making contact with a wearer's eyes or areas of the face around the eyes.

Referring to FIG. 3, each central portion 122*a,b* is also preferably curved outwardly away from the wearer's eyes. An outwardly curved central portion 122 may contour the eye safety frames 100 to the cheekbones of a wearer, allowing for a more comfortable and close fit to the wearer's face. The outward curve of the central portion 122 also provides an additional measure of protection against balls. As balls are generally spherical in shape, a portion of the ball may momentarily pass through the ocular space 104 of the eye safety frames 100 upon impact, even if the ball does not make contact with the wearer's eyes or surrounding area of the face. An outwardly curved central portion 122 of the bottom member 120 blocks the ball at a point farther from the wearer's face, thereby providing space for a portion of the ball to pass through the ocular space 104 without making contact with the wearer. By blocking the ball further from the wearer's face, the outwardly curved central portion 122 also allows for a larger ocular space 104, which may provide greater comfort and reduce any vision obstruction from the frames. Additionally, a central portion 122 that is constructed of a resiliently deformable material may absorb some of the energy of the impact with a ball. The outward curve of the central portion 122 facilitates this energy absorption by allowing the central portion 122 to temporarily deform inwardly towards a wearer's face before rebounding outwardly. Referring to FIG. 2, each bottom member 120*a,b* further includes a proximal inner segment 119*a,b* positioned between the proximal side member 116*a,b* and the central portion 122*a,b*. In the example illustrated, the proximal inner segment 119*a,b* is substantially straight in the vertical plane.

The distal side member 114, proximal side member 116, top member 118, and bottom member 120 may have varying thicknesses such that the shape of the ocular space 104 is different from the shape of the ocular frame portion 102. For example, the top member 118 may have a generally flat top side and a curved bottom side. In other examples the distal side member 114 may have a vertically oriented distal side an angled proximal side. In such an example, the ocular frame portion 102 may have a rectangular shape while the ocular space 104 may have a trapezoidal shape. In yet other examples, the bottom member 120 may have a central portion 122 that has a curved upper half and a flat lower half.

Figure 4:
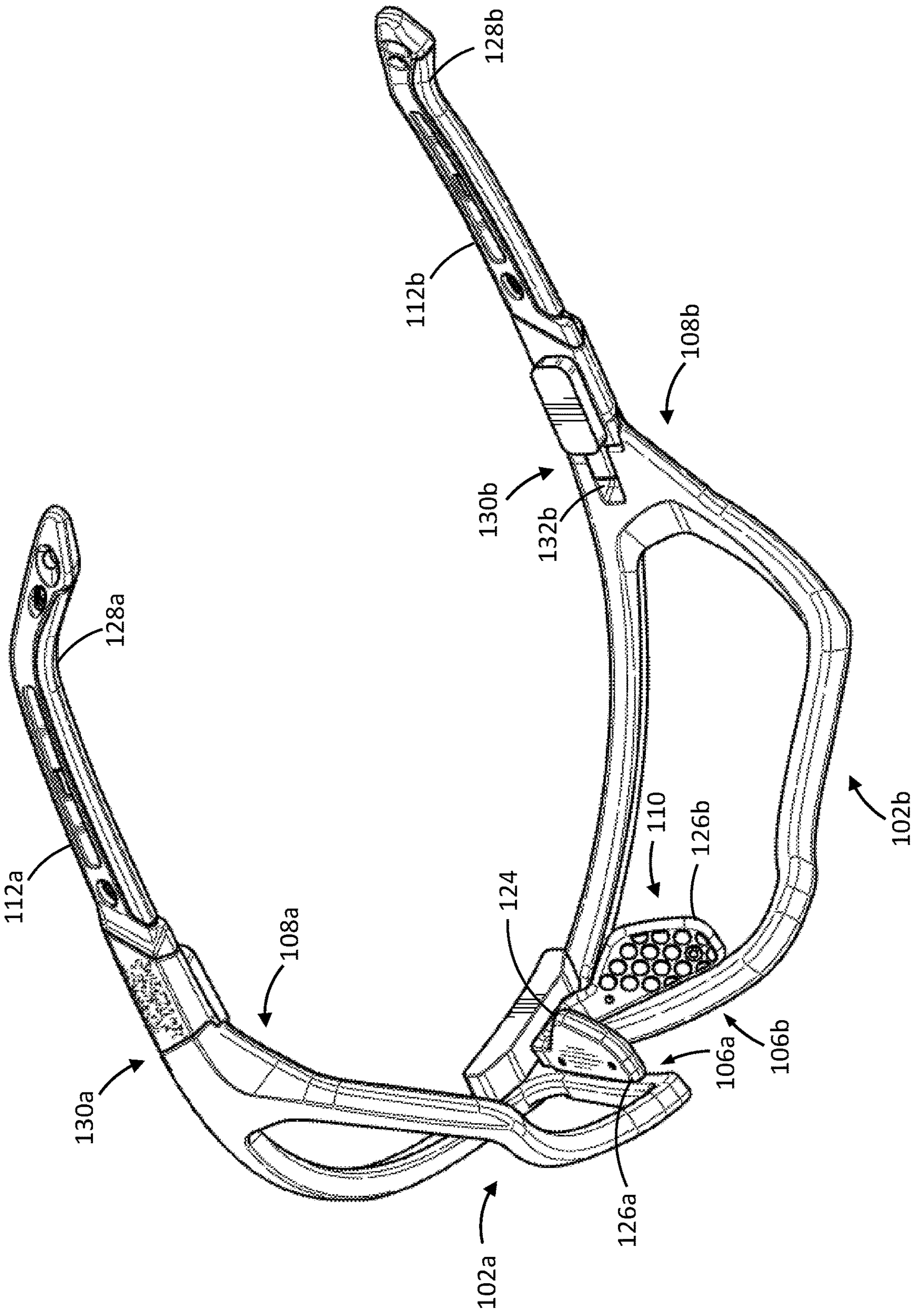
FIG. 4 is a bottom perspective view of the example eye safety frame shown in FIG. 1.

Referring now to FIGS. 1 and 4, the nose bridge portion 110 of the eye safety frame 100 is formed to sit on the bridge of a wearer's nose and facilitates maintaining the eye safety frames in a static position with respect to a wearer's head. The nose bridge portion 110 may be an adjustable nose bridge to accommodate various wearer nose sizes. The nose bridge portion 110 may have a central section 124 that connects the proximal portions 106*a,b* of each ocular frame portion 102*a,b*. The nose bridge portion 110 may also have a left adjustable nose wing 126*a* and a right adjustable nose wing 126*b*. The pair of adjustable nose wings 126*a,b* may extend downwardly and inwardly from the central section 124 and may be joined with the central section 124 by a malleable material. The malleable material may be bent to adjust the orientation of the nose wings 126*a,b* in relation to the central section 124.

Figure 5:
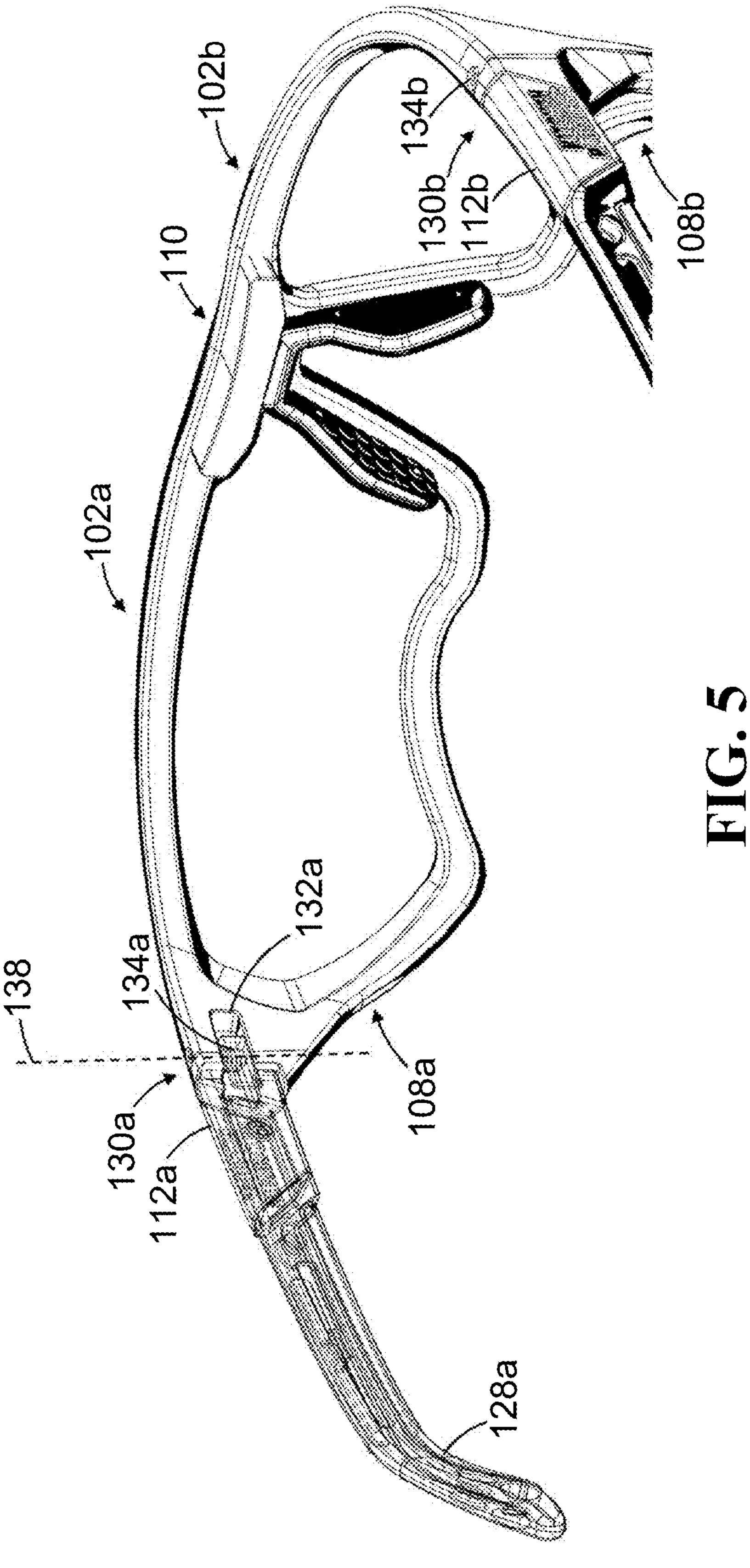
FIG. 5 is a side perspective view of the example eye safety frame shown in FIG. 1.

As illustrated in FIGS. 4 and 5, the left and right elongate arms 112*a,b* of the safety frame 100 extend rearwardly from the distal portions 108*a,b* of each ocular frame portion 102*a,b* towards a wearer's ears. The elongate arms 112*a,b* include curved portions 128*a,b* which wrap around the back of each of the wearer's ears and, along with the nose bridge portion 110, facilitate maintaining the eye safety frames 100 in a static position with respect to a wearer's head.

Furthermore, the elongate arms 112*a,b* may be connected to the distal portions 108*a,b* of each ocular frame portion 102*a,b* by a pair of pivot joints 130*a,b* which allow folding of each elongate arm 112*a,b*. In the illustrated example, the pivot joints 130*a,b* include a pair of slots 132*a,b* formed within the distal portions 108*a,b* which receive each of the elongate arms 112*a,b*, and a pair of pins 134*a,b* which pivotably connect each elongate arm 112*a,b* to the distal portions 108*a,b*. The pins 134*a,b* may define a vertically oriented pivot joint axis 138 about which the elongate arms 112*a,b* are rotatable between a folded and unfolded position. In the example illustrated, the pins 134*a,b* are threaded fasteners.

Figure 6:
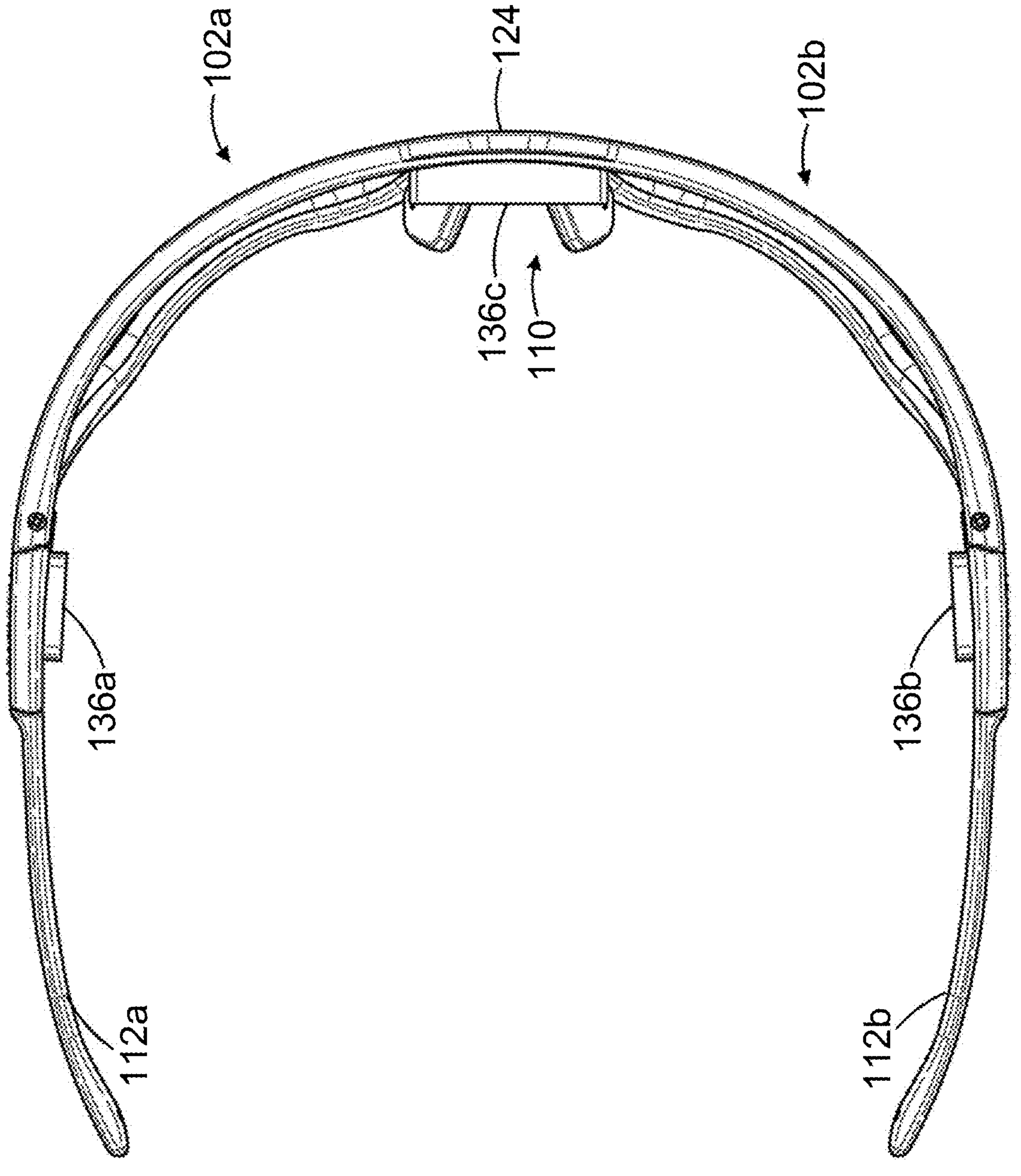
FIG. 6 is a top view of the example eye safety frame shown in FIG. 1.
Figure 7:
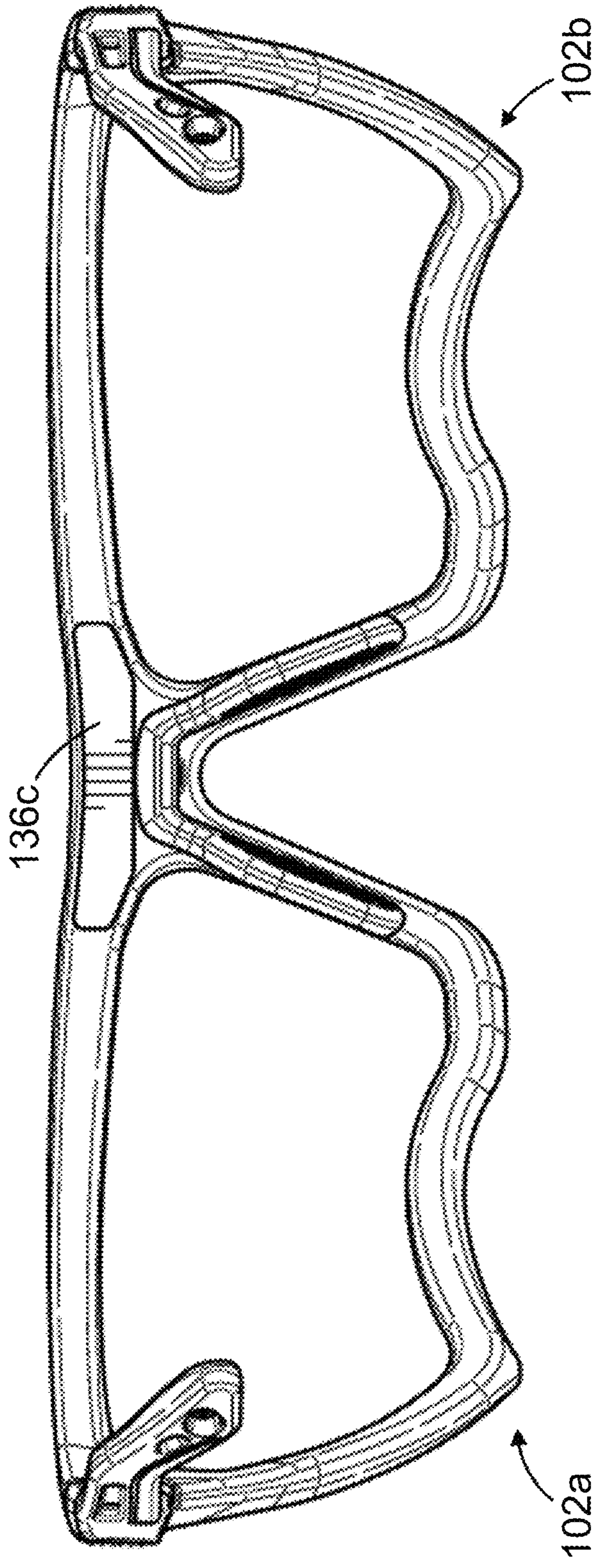
FIG. 7 is a rear view of the example eye safety frame shown in FIG. 1.

Referring now to FIGS. 6 and 7, the eye safety frame 100 may also include several resilient cushions 136*a,b,c* which are arranged at points of contact between the wearer's head and the eye safety frame 100. The cushions 136*a,b,c* may be made of a soft energy absorbing material such as foam or gel. In the example illustrated, a central cushion 136*c* extends inwardly from the nose bridge portion 110 towards a user's brow. When a ball impacts the front of the eye safety frame 100 it is pushed rearwardly into the wearer's face. The central cushion 136*c* may absorb some of the energy of the impact while providing a soft point of contact with the wearer's brow. Similarly, the illustrated example includes a left side cushion 136*a* and right side cushion 136*b* connected to a corresponding elongate arm 112 and extending inwardly in alignment with a wearer's temples. When an object, such as a ball, impacts the side of the eye safety frames 100 the left side cushion 136*a* and right side cushion 136*b* are adapted to absorb the energy of the impact and provide a soft point of contact with the wearer's temples.

In use, the lens less eye safety frames 100 provide an improved protection against ball impacts to a wearer's eyes and the surrounding area of the face. Unlike prior art safety glasses that contain a lens, the eye safety frames 100 do not require a lens that may become covered in debris or fog from the wearer's perspiration.

The curved central portion 122 of eye safety frame 100 reduces circular sections of the ocular space 104 while still maintaining a wearer's peripheral view on either side of the curved central portion 122. Maintaining lower peripheral viewing angles, for example when a wearer looks down and to the right or down and to the left, is critical for many sports. In racquet based sports such as pickleball, the ball is often travelling upwardly towards a wearer's left or right side, requiring the wearer to look down and to the left or down and to the right. An eye safety frame with a continuously narrow opening would require a wearer to physically move their head to see a ball in the lower periphery. In comparison, the curved bottom portion 122 allows a wearer to see the ball at these lower angles without moving their head.

As used herein, the wording "and/or" is intended to represent an inclusive or. That is, "X and/or Y" is intended to mean X or Y or both, for example. As a further example, "X, Y, and/or Z" is intended to mean X or Y or Z or any combination thereof.

While the above description describes features of example embodiments, it will be appreciated that some features and/or functions of the described embodiments are susceptible to modification without departing from the spirit and principles of operation of the described embodiments. For example, the various characteristics which are described by means of the represented embodiments or examples may be selectively combined with each other. Accordingly, what has been described above is intended to be illustrative of the claimed concept and non-limiting. It will be understood by persons skilled in the art that other variants and modifications may be made without departing from the scope of the invention as defined in the claims appended hereto. The scope of the claims should not be limited by the preferred embodiments and examples, but should be given the broadest interpretation consistent with the description as a whole.

The invention claimed is:

1. An eye safety frame for protecting a pair of eyes of a wearer from a ball, the wearer having a nose, ears, a brow, and temples, the frame comprising:

a pair of ocular frame portions, each ocular frame portion of the pair of ocular frame portions defining an ocular space configured to surround a corresponding one of the eyes;

each ocular frame portion of the pair of ocular frame portions comprising:

an elongate horizontal top member spaced apart from an elongate bottom member; the top and bottom members being joined by an elongate distal side member spaced apart from an elongate proximal side member, wherein the top member, the bottom member, the proximal side member, and the distal side member form a closed shape, the closed shape defining the ocular space, wherein the ocular space is uncovered;

wherein the bottom member comprises a central portion, wherein the central portion curves upwardly toward the top member and is configured to curve outwardly away from the corresponding one of the eyes, wherein the ocular space is configured to prevent the ball passing therethrough, wherein a length of the central portion is more than 50% of a length of the bottom member;

wherein a proximal portion of a first one of the ocular frame portions is joined to a proximal portion of a second one of the ocular frame portions by a nose bridge portion; and a pair of elongate arms, each one of the pair of arms extending from a distal portion of a corresponding one of the ocular frame portions and configured to extend toward a corresponding one of the ears.

2. The eye safety frame of claim 1, wherein the nose bridge portion comprises: a central section and a pair of adjustable nose wings extending from the central section, wherein the pair of adjustable nose wings are adapted to fit onto the nose.

3. The eye safety frame of claim 1, further comprising one or more resilient cushions extending inwardly from the eye safety frame.

4. The eye safety frame of claim 3, wherein the one or more resilient cushions are made from an energy absorbing material.

5. The eye safety frame of claim 4, wherein the one or more resilient cushions comprise a central cushion extending inwardly from the nose bridge and configured to extend towards the brow of the wearer.

6. The eye safety frame of claim 5, wherein the one or more resilient cushions comprise a pair of side cushions, wherein each elongate arm of the pair of elongate arms has an inner surface, and wherein each side cushion of the pair of side cushions is located on the inner surface of a respective one of the elongate arms and is configured to be adjacent to a respective temple of the user.

7. The eye safety frame of claim 1, wherein the bottom member further comprises a proximal inner segment located between the proximal side member and the central portion, wherein the proximal inner segment is substantially straight in a vertical plane.

* * * * *